US006302108B1

(12) United States Patent
Levine

(10) Patent No.: US 6,302,108 B1
(45) Date of Patent: Oct. 16, 2001

(54) SPERMICIDAL AND VIRICIDAL COMPOSITIONS

(75) Inventor: Ralph Levine, New York, NY (US)

(73) Assignee: Carter-Wallace, Inc, New York, NY (US)

( * ) Notice: Subject to any disclaimer, the term of this patent is extended or adjusted under 35 U.S.C. 154(b) by 0 days.

(21) Appl. No.: 09/523,029

(22) Filed: Mar. 10, 2000

(51) Int. Cl.$^7$ ........................................ A61F 6/06
(52) U.S. Cl. ............................... 128/830; 128/832
(58) Field of Search ................... 128/830–841, 128/842, 844

(56) References Cited

U.S. PATENT DOCUMENTS

| 4,587,268 | * | 5/1986 | Pfirrmuna | 514/774 |
| 5,617,877 | * | 4/1997 | Moench | 128/837 |

* cited by examiner

*Primary Examiner*—Michael A. Brown
(74) *Attorney, Agent, or Firm*—Kevin B. Clarke

(57) ABSTRACT

There is provided spermicidal/antiviral compositions in the form of lotions, cremes, foams and gels that are non-irritating. The compositions contain an effective amount of 4,4'-methylenebis-(tetrahydro-1,2,4-thiadiazine)-1,1,1',1'-tetraoxide as a spermicide/virucide.

4 Claims, No Drawings

SPERMICIDAL AND VIRICIDAL COMPOSITIONS

FIELD OF THE INVENTION

The present invention relates to spermicidal/antiviral compositions which can be used topically on the mucosal membrane or on any devices intended to contact body parts. More particularly, there is provided a non-irritating composition which is viricidal and spermicidal which can be used prophylactically.

BACKGROUND OF THE INVENTION

The population around the world is constantly coming in contact with viruses through social and/or accidental means. Those infected by the virus can in many cases be treated with conventional antivirals. However, some of the viruses such as hepatitis, HIV or herpes result in serious illnesses. Furthermore, many of the viruses mutate and become resistant to antibiotics. Therefore, it is desirable to kill the virus before the party is infected. It is therefore desirable to prophylactically protect a host from contamination by the virus.

The virus easily invades a host through mucous membranes or openings in the skin. The skin is generally a good barrier against invasion by microorganisms and washing can eliminate the microorganisms. However, there are times when a party who has come into contact with a microorganism cannot wash or treat an area of the body so that it is necessary to provide antiviral/spermicidal protection before and/or during contact in an area where infection can occur.

Due to the variety and complexity of the potential outcomes of sexual activity, including pregnancy, disease and discomfort, agents which can be used alone or in conjunction with condoms will require functionality that cannot reasonably be derived from a singular entity. For example, standard lubricants with detergents, specifically Nonoxynol-9 (N-9), provide protection against pregnancy and a variety of sexually transmitted diseases (STDs). The detergents also have a drawback in that in high concentrations and/or high frequency of use, they have the potential to cause irritation of mucosal tissue.

It is desirable to improve the efficacy of the agents while reducing the deleterious side effects. The primary focus is on strategies that can be used with or without condoms, but must address both pregnancy and disease prevention. There are other agents effective as spermicides and microbicides including other detergents, buffering agents and even selective inorganic agents. Combinations of these can increase the breadth of activity against STDs. For example, the use of buffering agents is highly effective against pregnancy, but of limited value in protection against STDs.

A third factor in the design of effective therapies includes the incorporation of agents selected to not only reduce possible irritation caused by one or more of the other agents, but to even ameliorate existing irritation.

One additional factor is to specifically include strategies directly targeting HIV. Due to the significance of HIV infection, specific agents should also be added to bolster the efficacy. Some of the agents already being considered for the amelioration of irritation are also effective binding agents for the same cell receptors that HIV targets. In addition, HIV-specific agents, while still in the early stages of testing, can be incorporated in future formulations.

In order for a composition to be capable of universal use it is required that it meet at least the following characteristics.

1. The composition is spermicidal/viricidal.
2. The composition can be used in sensitive areas, for example, mucosal membranes, therefore it must be non-irritating.
3. The composition must form a barrier.

Advantageously, the pH is adjusted for each site of use. There exists a specific need for improving methods and compositions for preventing sexually transmitted diseases (STDs) and unwanted pregnancies both with and without condoms. This objective should be realized by maintaining normal and protective vaginal flora that play a role in the prevention of vaginitis, vaginosis, and urinary tract infections. The present invention is also based on the realization that a method providing rapid and reliable control of vaginal pH could provide a highly effective, yet highly physiologic means to achieve these goals.

The most effective contraceptive methods (sterilization, intrauterine devices, and contraceptive hormones) provide no protection against STDs. Barrier contraceptive methods such as condoms, diaphragms, and vaginal spermicides help prevent STD transmission by interposing a mechanical or chemical barrier between the female and the male, most importantly between the uterine cervix and the glans and urethral orifice of the penis. This barrier action is effective because secretions from the sites (cervical mucus and semen) are the most important sources of STD pathogens and also because these sites are the most susceptible targets for many STD pathogens. However, current barrier methods suffer from poor acceptance and therefore poor efficacy because they are inconvenient to use, and/or have undesirable toxicity. Male and female condoms are cumbersome to use and may reduce sexual pleasure and intimacy. Vaginal spermicides can erode the mucosa if used too frequently, and even with infrequent use, can disrupt the protective normal vaginal flora.

The pH of a healthy vagina is mildly acidic (pH 3.5–4.5) and this acidity is thought to be generated by the production of lactic acid by lactobacilli, which form a major component of the healthy vaginal flora. Together with other factors, this acid pH is widely recognized to prevent overgrowth of undesirable microbes (Candida, harmful anaerobes, and bacteria that may cause urinary tract infections) and encourages the continued dominance of lactobacilli which, in addition to mild acidity, provide other protective mechanisms such as production of hydrogen peroxide.

It is also known that sperm are inactivated by the mild acidity of the healthy vagina, and acid substances have been used as home made vaginal contraceptives for centuries. More recently it has been recognized that many sexually transmitted disease pathogens, Neisseria gonorrhea, Treponema palladium, Haemophilus ducreyi, and most or all enveloped STD viruses including herpes simplex virus, cytomegalovirus, and human immunodeficiency virus, are also inhibited or inactivated by mild acidic pH. However, semen contains a potent alkaline buffering capacity that neutralizes the vaginal acidity for a period of many hours after intercourse. This alkaline buffering capacity enables sperm to swim from the vagina into the cervix and upper genital tract.

Unfortunately, STD pathogens in genital secretions can also exploit this period of neutral vaginal pH, since it allows time for them to reach and infect their target cells. If this semen-induced neutralization of vaginal acidity could be promptly and reliably overcome, both contraception and STD prevention could be achieved by a method that closely mimics the normal physiological state of the vagina.

In addition, the elevated pH also allows certain strains of Staphylococcus aureus to produce shock toxin I, whereas production of this toxin is completely inhibited at acidic pH≦5.0. Thus, loss of protective acidity may result in staphylococcal toxic shock syndrome, candida vaginitis, bacterial vaginosis, or urinary tract infection.

The use of cellulosic binders such as methyl cellulose, hydroxymethylcellulose, and the like in mucosal areas can cause irritation over long periods of time.

U.S. Pat. No. 5,617,877 to Moench et al. discloses a contraceptive composition comprising a spermicide and cellulosic delivery system over which the present invention provides an advantage.

SUMMARY OF THE INVENTION

The present invention provides spermicidal/antiviral composition for use topically and in mucosal areas of the body. The composition comprises:

(a) an effective amount of 4,4'-methylenebis-(tetrahydro-1,2,4-thiadiazine)-1,1,1',1'-tetraoxide; and (b) a buffer in an effective amount for maintaining the pH of the composition at a proper pH for the area of application.

Advantageously, when the composition is used in mucosal areas the pH is about 3.5–4.5.

The composition can be formulated as a creme, lotion, gel, foam, and the like.

It is therefore an object of the invention to provide a spermicidal/antiviral composition for use on mucosal membrane or on any device intended to contact body parts.

It is a further object of the invention to provide both an anti-viral and spermicidal composition which can prevent STD.

It is yet another object of the invention to provide a composition to prevent STD for use with condoms and the like.

These objects and other advantages of the invention will be better understood from a reading of the description of preferred embodiments and the examples.

DESCRIPTION OF THE PREFERRED EMBODIMENTS

The novel spermicidal and viricidal compound employed in the compositions of the present invention is 4,4'-methylenebis-(tetrahydro-1,2,4-thiadiazine)-1,1,1',1'-tetraoxide, commonly known as taurolidine. It has been found that taurolidine is effective in preventing pregnancy as well as the transmission of AIDS, herpes, hepatitis B, cytomegalovirus, chlamydia, trichomonas, various bacteria inducing gorrhoea and G vaginalis and test strain of treponema phagedenis, a surrogate of syphilis.

Taurolidine occurs as a white to off-white powder having the molecular formula $C_7H_{16}N_4O_4S_2$.

Taurolidine's general characteristics include acceptable stability in the solid state when stored at ambient conditions, melting with decomposition at approximately 170° C. and the following solubility in aqueous solutions and organic solvents.

| Water | 1% at 20° C. |
|---|---|
| Dilute HCl | soluble |
| Dilute NaOH | soluble |

-continued

| CHCl$_3$ | insoluble |
|---|---|
| EtOH | sparingly soluble |
| DMF | 1 g in 2 mL/ca. 60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including U.S. Pat. No. 3,423,408; Switzerland No. 482,713 and United Kingdom No. 1,124,285 and is carried out in five stages:

Potassium phthalimidoethane sulphonate is prepared from taurinc, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in co-pending U.S. patent application Ser. No. 09/151,885 filed Sep. 11, 1998 and in U.S. Pat. No. 3,423,408 and elsewhere in the literature. In addition, the following United States Patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine's mechanism of action unlike that of known virucides is based on a chemical reaction. While not being bound by any theory, during the metabolism of taurolidine to taurinamide and ultimately taurine and water, methylol groups are liberated which chemically react with the protein in the walls of the virus this results in the destruction of the protein coat protecting the single nucleic acid which makes up the virus.

Taurolidine has been shown to be safe and well tolerated at systemic doses exceeding 40 g/day and cumulative doses up to and exceeding 300 g.

It has long been the goal of the pharmaceutical industry to produce antibiotic and antiviral medicinal substances that have the power to kill—or at least to arrest the growth of—many disease causing viruses and mycobacteria such as sexually transmitted diseases.

In general, the compositions of the present invention can be readily utilized in topical pharmaceutical formulations preferably formulations in gel, creme or ointment form.

The formulations of taurolidine generally utilized are sterile solutions containing about 0.5%, 1.0%, 2.0% or about 4.0% taurolidine.

Application of the compositions of the present invention may be introvaginally, however, the compositions may also be applied to latex or other condoms as well as other barrier contraceptive devices.

The aqueous gels of the invention, especially those containing highly carboxylated polymers have a further utility as a sexual lubricant capable of preventing the exchange or transmission of STD pathogens and sperm during sexual activity.

When formulated as a lubricant, the compositions can be applied to external genitalia as well as internal mucosal surfaces to reduce microtrauma resulting from inadequate lubrication will also prevent transmission of viable STD pathogens through traumatized, disease or healthy skin or mucosa.

In a known manner, the composition of the invention may also contain adjuvants which are customary in the pharmaceutical or cosmetic field, such as hydrophilic or lipophilic gelling agents, hydrophilic or lipophilic active agents, preservatives, buffers, antioxidants, solvents, perfumes and fillers. The amounts of these different adjuvants are those traditionally used in the pharmaceutical or dermatological field, and are, for example, from 0.01% to 10% of the total weight of the composition.

As hydrophilic gelling agents, carboxyvinyl polymers (Carbomer®), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantonin, sugars and sugar derivatives, water-soluble vitamins, starch and plant extracts, in particular those of Aloe vera may be used.

As lilophilic active, agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include plant or herbal extracts. For example, there may be utilized extracts of Paraguay tea, Kola and Guarana, which provide a source of methylxanthines, saponius, tannins and glycosides that have been shown to be anti-inflammatory and can be used to treat or prevent irritations. The extract of Paraguay tea is known as "Mate extract" and is described in the "International Cosmetic Ingredient Dictionary," 5$^{th}$ Edition. Mate extract is commercially available in combination with extracts of Kola and Guarana which is sold by Cosmetic Ingredient Resources of Stamford, Connecticut under the trademark "QUENCHT."

Each of mate extract, serine protease inhibitor and aloe vera extract are known to provide anti-inflammatory activity. The anti-elastase and anti-tryptase activity of the protease inhibitor has been shown to provide a synergistic effect in treating skin inflammations.

Up to 10% by weight of zinc salts can be used to prevent irritations when required. Suitable zinc salts include zinc gluconate, zinc acetate, zinc chloride, etc.

The preferred embodiment of the present invention covers the use of the spermicidal/viricidal composition in combination with condoms formed of linear chain, aliphatic polyether-based polyurethanes, which are synthesized from the solid phase polymerization reaction of methylene bis(4-cyclohexylisocyanate) and polytetramethylene ether glycol of about 2000 molecular weight which is chain extended/terminated with 1,4-butanediol. The elastomers are clear and because of their aliphatic nature will not yellow upon aging nor upon exposure to oxygen or ultraviolet light.

The polyurethane elastomers are dissolved in a solvent preferably tetrahydrofuran in order to prepare the dip solution for condom manufacture. The only other additive to the dip solution, at a very low level, is a mold release agent such as a silicone fluid (polydimethylsiloxane-polyoxyethylene copolymer) which will facilitate removal of the formed condom from the mandrels.

Example 1, which follows, sets forth a polyurethane condom formulation for use in the present invention.

EXAMPLE 1

| Ingredient | W/W |
|---|---|
| Tetrahydrofuran | 89.45% |
| Polyether polyol aliphatic diisocyanate | 10.53% |
| Silicone Fluid | 0.02% |
| | 100.00% |

A preferred method for manufacturing the polyurethane elastomer condoms is fully described in copending commonly assigned U.S. patent application Ser. No. 09/095,330 filed Jun. 10, 1998.

The primary process in the manufacture of the polyurethane elastomer condom is the condom forming or dipping process. The following are the process control parameters for the dipping process:

| | |
|---|---|
| Dipping Chamber Atmosphere | Temperature 50–70° F., Filtered (maximum 100 mM mesh) recirculating nitrogen atmosphere. |
| Dip Tank | Temperature 50–55° F. controlled by passing recirculated dipping solution through a heat exchanger system; Viscosity 100–300 cps (depending upon molecular weight distribution of the polymer) controlled by automated viscometer system on closed loop from feed and dip tanks; the automated dipping solution level control system provides control of particulate matter and maintains viscosity and temperature uniformity of the dip solution which is recirculated at 40–50 gallons per minute through a 25–50 mM bag-type filter. |
| Film Drying Station 1 | Temperature 90–115° F., air flow approximately 1000 F/M (feet per minute) filtered (maximum 100 mM mesh) recirculating nitrogen atmosphere. |
| Film Drying Station 2 | Temperature 135–152° F., air flow approximately 1000 F/M filtered (maximum 100 mM mesh) recirculating nitrogen atmosphere. |
| First Chill Station | Temperature 50–55° F., air flow approximately 750 F/M filtered (maximum 100 mM mesh) recirculating nitrogen atmosphere. |
| Second Chill Station | Temperature 45–50° F., air flow approximately 750 F/M filtered (maximum 100 mM mesh) recirculating nitrogen atmosphere. |
| Third Chill Station | Temperature 30–40° F., air flow approximately 750 F/M filtered (maximum 100 mM mesh) recirculating nitrogen atmosphere. |

The dipping section of the manufacturing equipment operates as noted above in a nitrogen gas environment that is isolated from the cleaning/take-off section of the dipping line by means of an air lock. This air lock not only minimizes infiltration of oxygen in the dipping section of the line but also aids in controlling particulate matter. A cover on the dip tank also helps to prevent any contamination. THF that evaporates from the dip tank and mandrels is recovered for re-use. An in-line analyzer monitors water and stabilizer content of the recovered THF for suitability prior to re-use.

The second section of the condom production line is composed of the condom take-off and form cleaning section. The process control parameters are as follows:

| | |
|---|---|
| Former Wash Station | Temperature up to 160° F.; wash solution is recirculated through a 25–50 mM bag-type filter. |
| Former Rinse Station | Temperature up to 160° F.; rinse solution is recirculated through a 25–50 mM bag-type filter. |
| Former Drying Oven | Temperature 160° F.; air flow approximately 1000 F/M filtered (maximum 100 mM mesh) recirculated air. |

After completion of the dipping and drying operations, the condoms are removed from the mandrel. Condoms coming off the dipping line are collected and sampled for evaluation of mass, dimensions (ring thickness, length and film thickness) and visual defects (folds, creases, etc.) and testing for holes.

The condoms are then rolled around the ring to form a cup-shaped elastic ring of predetermined size and circumference. The result is several layers of polyurethane elastomer being rolled around the thickened ring formed at the top, open end, of the sheath forming a cup within the circumference of the ring. In this form, the condom is easily mountable for use during sexual intercourse and lubricants and the spermicide/viricide of the present invention are added to the cup-shaped polyurethane elastomer sheath, in a well known manner.

Example 2, which follows, sets forth the spermicidal/viricidal gel suitable for addition to the polyurethane condom

EXAMPLE 2

| | |
|---|---|
| Deionized water | 97.69 WT % |
| 4,4'-methylenebis(tetrahydro-1,2,4-thiadiazine) 1,1,1',1'-tetraoxide | 2.00 WT % |
| *Carbomer | 0.31 WT % |

*Carbopol 940 BF Goodrich Performance Materials Richfield, Ohio

The carbomer is dusted into the water with mixing and the mixture heated to about 65°–70° C. The 4,4'-methylenebis-(tetrahydro-1,2,4-thiadiazine)-1,1,1',1'-tetraoxide is added with mixing and the mixture cooled to about 40° C.

One to two grams of the aqueous gel prepared in a manner described in Example 2 are added to the cup shaped elastomer of Example I in order to provide spermicidal/viricidal activity during intercourse. Alternatively, the gel may be applied directly to the mucosal areas.

I claim:

1. A method for the prevention of pregnancy and the transmission of sexually transmitted viruses and other infection comprising introvaginally applying an effective amount of 4,4'-methylenebis-(tetrahydro-1,2,4-thiadiazine)-1,1,1', 1'-tetraoxide.

2. A spermicidal composition comprising 4,4'-methylenebis-(tetrahydro-1,2,4-thiadiazine)-1,1,1',1'-tetraoxide.

3. The composition of claim 2 applied to a condom or other barrier device.

4. The composition of claim 2 applied to the mucosal area.

* * * * *

UNITED STATES PATENT AND TRADEMARK OFFICE
CERTIFICATE OF CORRECTION

PATENT NO.    : 6,302,108 B1
DATED         : October 16, 2001
INVENTOR(S)   : Ralph Levine It is certified that error appears in the above-identified patent and that said Letters Patent is hereby corrected as shown below:

<u>Title page,</u>
Add Item:

-- Related U.S. Application Data

[60] Provisional Application No. 60/124,534, filed on March 12, 1999. --

Signed and Sealed this

Eighteenth Day of March, 2003

JAMES E. ROGAN
*Director of the United States Patent and Trademark Office*